United States Patent [19]

Adams et al.

[11] Patent Number: 4,968,821

[45] Date of Patent: Nov. 6, 1990

[54] 4,7-BENZOFURANDIONE DERIVATIVES

[75] Inventors: Julian Adams, Westmount; Yvan Guindon, Montreal; Patrice C. Belanger, Dollard des Ormeaux; Michel L. Belley, St. Laurent; Joshua Rokach, Laval, all of Canada

[73] Assignee: Merck Frosst Canada, Inc., Kirkland, Canada

[21] Appl. No.: 217,264

[22] Filed: Jul. 11, 1988

Related U.S. Application Data

[62] Division of Ser. No. 64,152, Jun. 18, 1987, Pat. No. 4,778,805.

[51] Int. Cl.$^5$ .......................................... C07D 307/78
[52] U.S. Cl. .................................................. 549/468
[58] Field of Search .......................... 514/469; 549/468

[56] References Cited

U.S. PATENT DOCUMENTS 4,663,347  5/1987  Atkinson et al. .................... 514/469
4,778,805  10/1988  Adams et al. ........................ 549/362

OTHER PUBLICATIONS

Morrison et al., "Organic Chemistry", Allyn and Bacon, Inc., Boston, Fifth Edition, 1987, p. 1092.

*Primary Examiner*—John C. Bleutge
*Assistant Examiner*—Vasu S. Jagannathan
*Attorney, Agent, or Firm*—Gabriel Lopez; Hesna J. Pfeiffer

[57] ABSTRACT

4,7-Benzofurandione derivatives of Formula I, pharmaceutical compositions, and methods of treatment are disclosed. These compounds are useful as inhibitors of mammalian leukotriene biosynthesis. As such, these compounds are useful therapeutic agents for treating allergic conditions, asthma, cardiovascular disorders, inflammation, psoriasis and allergic conjunctivitis. The compounds are also useful as analgesics and as cytoprotective agents. Also disclosed are novel intermediates useful for the preparation of the 4,7-benzofurandiones of this invention.

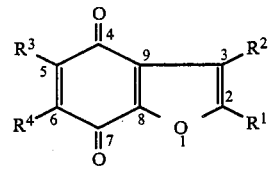

1 Claim, No Drawings

4,7-BENZOFURANDIONE DERIVATIVES

BACKGROUND OF THE INVENTION

This is a division of Ser. No. 64,152, Jun. 18, 1987, now U.S. Pat. No. 4,778,805.

U.S. Pat. No. 4,778,805, Adams et al., is incorporated herein in its entirety.

SUMMARY OF THE INVENTION

It has now been discovered that certain tetrasubstituted benzofurandiones of Formula I are effective inhibitors of leukotriene biosynthesis. Thus, these compounds are useful therapeutic agents for treating allergic conditions, asthma, cardiovascular disorders such as angina, inflammation, for amelioration of skin diseases like psoriasis and atopic eczema, for treatment of allergic conjunctivitis, as analgesics, and as cytroprotective agents.

DETAILED DESCRIPTION OF THE INVENTION

The compounds of the present invention are compounds of the formula:

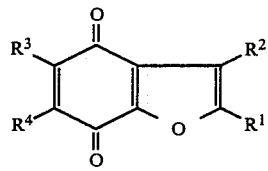

I $R^1$ is $-(CR^5R^5)_l-(X^1)_m-(CR^5R^5)_n-$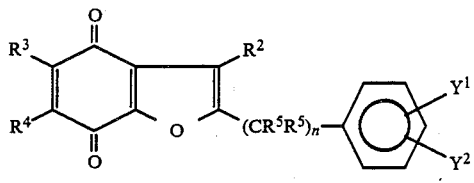;

$-(CR^5R^5)_s-(X^1)_t-(CR^5R^5)_u-CO_2R^6$; or lower alkyl;

$R^2$ is lower alkyl;

$R^3$ and $R^4$ are each independently $R^2$, Cl, $X^2R^2$, or $X^3R^5$;

$R^5$ is H or lower alkyl, or two $R^5$'s when attached to N may be joined to form a 5- or 6-membered ring;

$R^6$ is H or lower alkyl;

$R^7$ is H or lower alkyl;

$R^8$ is H or lower alkyl;

$X^1$ is $X^2$ or $X^3$;

$X^2$ is S, S(O), S(O)$_2$;

$X^3$ is O or $NR^5$;

$X^4$ is $X^2$ or $X^3$ $Y^1$ and $Y^2$ are each independently: H, $R^2$, $X^2R^2$, $X^3R^5$, halogen, $(X^4)_w-(CR^5R^5)_z-CO_2R^7$, $CF_3$, $COR^8$, $CONR^5R^5$, or $S(O_2)NR^5R^5$; or $Y^1$ and $Y^2$ may be joined to form a 5- or 6-membered ring, containing one or two O atoms, such as $-OCH_2O-$, $-OCH_2CH_2O-$, $-OCH_2CH_2-$ or $-OCH_2CH_2CH_2-$;

l and n are each independently 0 to 5;

m is 0 to 1;

s is 0 to 3;

u is 0 to 3 provided that when t is 1 and $R^6$ is H, then u is 1 to 3;

t is 0 or 1;

w is 0 or 1; and z is 0 to 3, provided that when w is 1 and $R^7$ is H, then z is 1 to 3;

and the pharmaceutically acceptable salts thereof.

A preferred embodiment of the present invention is represented by Formula Ia:

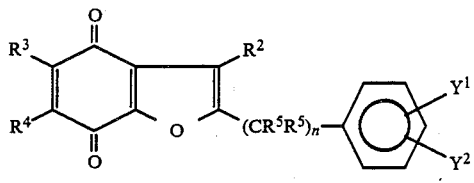

Ia wherein:

$R^3$ is $R^2$ $R^4$ is $R^2$ or $X^3R^5$ n is 0 or 1 and the remaining substuents are as defined for Formula I.

Another preferred embodiment of the present information is that wherein:

$R^1$ is lower alkyl;

$R^3$ and $R^4$ are each independently $R^2$, $X^2R^2$, or $X^3R^5$;

and the remaining substituents are as defined for Formula I.

A further embodiment of this invention are novel di- and tri-substituted compounds of Formula Ib useful as intermediate for the preparation of Formula I compounds. These compounds are represented in Table 2.

TABLE 2

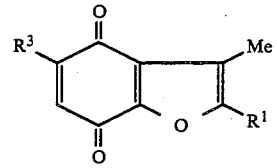

Ib

| Ex. No. | $R^1$ | $Y^1$ | $Y^2$ | $R^3$ |
|---|---|---|---|---|
| 25 | CO$_2$Et | — | — | H |
| 26 | CO$_2$Et | — | — | n-Pr |
| 27 | H | — | — | n-Pr |
| 28 | CH$_2$C$_6$H$_3$Y$^1$Y$^2$ | 4-OMe | H | n-Pr |
| 29 | CH$_2$C$_6$H$_3$Y$^1$Y$^2$ | 4-OH | H | n-Pr |
| 30 | CH$_2$C$_6$H$_3$Y$^1$Y$^2$ | 4-OMe | H | H |
| 31 | CH$_2$CO$_2$Et | — | — | n-Pr |

What is claimed is:

1. A compound of the Formula Ib:

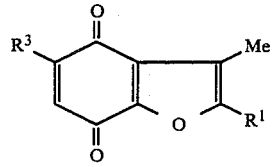

Ib

| $R^1$ | $Y^1$ | $Y^2$ | $R^3$ |
|---|---|---|---|
| CO$_2$Et | — | — | H |
| CO$_2$Et | — | — | n-Pr |
| H | — | — | n-Pr |
| CH$_2$C$_6$H$_3$Y$^1$Y$^2$ | 4-OMe | H | n-Pr |
| CH$_2$C$_6$H$_3$Y$^1$Y$^2$ | 4-OH | H | n-Pr |
| CH$_2$C$_6$H$_3$Y$^1$Y$^2$ | 4-OMe | H | H |
| CH$_2$CO$_2$Et | — | — | n-Pr |

* * * * *